United States Patent
Hua (10) Patent No.: US 6,576,457 B1
(45) Date of Patent: Jun. 10, 2003

(54) FUNGAL MEDIA AND METHODS FOR CONTINUOUS PROPAGATION OF VESICULAR-ARBUSCULAR MYCORRHIZAL (VAM) FUNGI IN ROOT ORGAN CULTURE

(75) Inventor: Sui-Sheng T. Hua, Orinda, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/737,975

(22) Filed: Dec. 15, 2000

(51) Int. Cl.$^7$ ................................................. C12N 1/18
(52) U.S. Cl. ............................... 435/256.8; 435/254.1; 47/1.1; 71/5
(58) Field of Search ........................ 435/256.8, 254.1; 47/1.1; 71/5

(56) References Cited

U.S. PATENT DOCUMENTS

| | | | |
|---|---|---|---|
| 3,011,951 A | * 12/1961 | Murray | ........................ 435/56 |
| 4,144,133 A | 3/1979 | Dorn et al. | |
| 4,294,037 A | 10/1981 | Mosse et al. | |
| 4,550,527 A | 11/1985 | Hall et al. | |
| 4,551,165 A | 11/1985 | Warner | |
| 4,599,312 A | 7/1986 | Mugnier et al. | |
| 4,945,059 A | 7/1990 | Okii et al. | |
| 5,002,603 A | 3/1991 | Safir et al. | |
| 5,075,332 A | 12/1991 | Haglund | |
| 5,096,481 A | 3/1992 | Sylvia et al. | |
| 5,125,955 A | 6/1992 | Safir et al. | |
| 5,178,642 A | 1/1993 | Janerette | |
| 5,262,381 A | 11/1993 | Tuse +e,uml +ee et al. | |
| 5,344,471 A | 9/1994 | Tüse et al. | |
| 5,554,530 A | 9/1996 | Fortin et al. | |

FOREIGN PATENT DOCUMENTS

EP    0 209 627 A2    1/1987

OTHER PUBLICATIONS

The Merck Index, p. 1271, 1996.*
Bécard, G. et al., "Early events of vesicular–arbuscular mycorrhiza formation on Ri T–DNA transformed roots," *New Phytol.*(1988) 108:211–218.
Chabot, S. et al, "Life Cycle of *Glomus Intraradix* in Root Organ Culture," *Mycologia* (1992) 84(3):315–321.
Dehne, H.W., "Interaction Between Vesicular–Arbuscular Mycorrhizal Fungi and Plant Pathogens," *Phytopathology* (1982) 72(8):1115–1119.

Douds, Jr., D.D., "A procedure for the establishment of *Glomus mosseae* in dual culture with Ri T–DNA–transformed carrot roots," *Mycorrhiza* (1997) 7:57–61.
Harrison, M.J., "Molecular and Cellular Aspects of the Arbuscular Mycorrhizal Symbiosis," *Annu. Rev. Plant Physiol. Plant Mol. Biol.* (1999) 50:361–389.
Hernández–Sebastià, C. et al., "Water relations of whole strawberry plantlets in vitro inoculated with *Glomus intraradices* in a tripartite culture system," *Plant Sciences* (1999) 143:81–91.
Mugnier, J. et al., "Vesicular–Arbuscular Mycorrhizal Infection in Transformed Root–Inducing T–DNA Roots Grown Axenically," *Phytopathology* (1987) 77(7):1045–1050.
Nuutila, A.M. et al., "Infection of hairy roots of strawberry (*Fragaria x Ananassa* Duch.) with arbuscular mycorrhizal fungus," *Plant Cell Reports* (1995) 14:505–509.
Rousseau, A. et al., "Mycoparasitism of the Extramatrical Phase of *Glomus intraradices* by *Trichoderma harzianum*," *Phytopathology*(1996) 86(5):434–443.
Ruehle, J.L. et al., "Fiber, Food, Fuel, and Fungal Symbionts," *Science* (1979) 206:419–422.
St–Arnaud, M. et al., "Enhanced hyphal growth and spore production of the arbuscular mycorrhizal fungus *Glomus intraradices* in an in vitro system in the absence of host roots," *Mycol. Res.* (1996) 100(3):328–332.
Schreiner, R.P. et al., "Stimulation of Vesicular–Arbuscular Mycorrhizal Fungi by Mycotrophic and Nonmycotrophic Plant Root Systems," *Applied and Environmental Microbiology* (1993) 59(8):2750–2752.
Wang, H. et al., "Vesicular–arbuscular Mycorrhizal Peat–based Substrates Enhance Symbiosis Establishment and Growth of Three Micropropagated Species," *J. Amer. Soc. Hort. Sci.* (1993) 118(6):896–901.

* cited by examiner

Primary Examiner—Irene Marx
(74) Attorney, Agent, or Firm—Margaret A. Connor; Thanda Wai; John Fado (57) ABSTRACT

An in vitro system using Agrobacterium-transformed dicotyledon roots (such as carrot roots) and vesicular-arbuscular mycorrhizal fungi (such as Glomus intradices) was developed to produce viable and aseptic spores. The entire life cycle from the growth of initial germ tubes to the formation of external mycelium network and spore production was observed nondestructively using light microscopy. The system may be subcultured continuously for the production of viable and clean spores.

5 Claims, 7 Drawing Sheets

FUNGAL MEDIA AND METHODS FOR CONTINUOUS PROPAGATION OF VESICULAR-ARBUSCULAR MYCORRHIZAL (VAM) FUNGI IN ROOT ORGAN CULTURE

FIELD OF THE INVENTION

The invention relates to novel fungal growth media and methods for the in vitro aseptic mass production of endomycorrhizal fungal propagules, mainly spores, using transformed root organ culture.

BACKGROUND OF THE INVENTION

Vesicular-arbuscular mycorrhizal (VAM) fungi form beneficial symbiotic associations with roots of a wide range of plants (Harley and Smith, 1983). The term "mycorrhiza," which literally means "fungus root," was first used in 1885 by A. B. Frank to describe the intimate associations between fungal hyphae and the roots of forest trees. The hyphae of VA mycorrhizal fungi penetrate and form arbuscules within root cortical cells and intercellular vesicles, but the external hyphae extend further into the soil for mineral nutrient uptake. A simple interpretation of mycorrhizal symbiosis is that the plant supplies carbon compounds to increase fungal growth and the plant benefits by having its root system effectively extended. The surface area of fungal hyphae can be much greater than that of the plant roots (Smith and Gianinazzi-Pearson; 1992, Smith and Read, 1997).

The importance of VA mycorrhizae in the growth and nutrition of plants has recently been reviewed (Gianinazzi and Schhepp, 1994; Smith and Read, 1997; Harrison, 1999). On soils low in available phosphate, the improved growth observed in VA mycorrhizal plants compared with uninoculated controls is thought to be due largely to an improved supply of phosphate. The external hyphae in soil absorbs non-mobile nutrients such as phosphate (P), potassium ($K^+$), and ammonium ($NH_4^+$) beyond the root zone and transfer phosphate from the fungus to the root cells. Thus, any process that was previously limited by the availability of phosphate will increase in rate. Improved phosphate nutrition, as well as direct fungal effects, may be implicated in the enhanced uptake of other macronutrients and micronutrients by plants.

Many VA mycorrhizal plants have increased resistance to disease compared to non-mycorrhizal controls, although the converse has also been reported. It has been suggested that physical protection of potential entry points on the root surface by the mycorrhizal fungi, and the reduced availability of carbon compounds to pests and pathogens (due to their being used by the fungi) are responsible for increased resistance to some diseases; however, the improved nutritional status of mycorrhizal plants made them more susceptible to other diseases (Pfleger and Linderman, 1994; Podila and Dodds,1999). A positive role for VA mycorrhizae in plant protection is indicated by the presence of phytoalexins (compounds involved in resistance to infection by pathogens), for example in mycorrhizal soybean roots (Morandi et al., 1984; Morandi, 1989; Harrison, 1999).

Certain changes in the plant hormonal balance have been shown to be related to a VA mycorrhizal effect. Some VA endomycorrhizae have been shown to contain elevated levels of phytohormones compared with non-infected roots. This may be due to the improved supply of nutrients, but could equally well be a direct result of the fungus, as it has been reported that plant growth promoting substances have been detected in germinating VA mycorrhizal fungal spores. Hormone accumulation in host tissue is affected by mycorrhizal infection, with changes in the levels of cytokinin, abscisic acid, and gibberellin-like substances and alteration in biomass partitioning (Barker et al., 1998; Danneberg et al., 1992; Dixon, 1992; Goicoechea, 1996).

The effect of VAM fungal infection on the drought resistance of plants is probably also due to the improvement of nutrient uptake. A mycorrhizal pathway of nutrient acquisition would become much more important in dry soil, because the nutrients become much less mobile. There seems little doubt that, like plant growth changes, mycorrhizal fungi can cause changes in plant water relations and may, at least in some cases, improve drought resistance of the plant (Al-Karaki et al., 1998; Goicoevhea et al., 1996; Nelson, 1987).

Morton and Benny (1990) described 149 species of VAM fungi. The VA mycorrhizal fungi are all classified as belonging to the family Endogonaceae possessing coenocytic hyphae (with only rare septa or none at all), which contain many nuclei. They have not propagated independently from host plant roots, and no sexual reproduction has observed, although both have been demonstrated in some non-mycorrhizal, saprophytic members of the Endogonaceae. Genera known to form VA mycorrhizae are Glomus, Gigaspora, Acaulospora, Sclerocystis, and Entrophospora. Knowledge of the phylogenetic relationships of VAM fungi is fragmentary. There is scant literature available on cytological or sexual processes involved in spore formation for these fungi. The taxonomic position of the VAM fungi is, therefore, inferred from developmental processes and spore morphology (Schenck and Yvonne, 1992; Morton, 1995).

The VA mycorrhizal fungi produce large vegetative spores (often greater than 100 $\mu$m in diameter) usually on hyphae external to the roots. The genera have been classified according to the appearance of the spores. Spores may be recovered from the soil around infected plants by wet-sieving through a series sieves of different sizes, ranging from 1,000 $\mu$m to 75 $\mu$m. Either spores or fragments of infected roots may be used to inoculate further plants. Spores produced by Gigaspora, Acaulospora, and Entrophospora are called azygospores. Spores produced by Glomus and Sclerocystis, termed chlamydospores, are presumably asexual, thick-walled resting cells. Additional morphological characters that are useful in separating genera and species of VAM fungi are (i) the method of spore germination; (ii) presence or absence of sporocarps; (iii) presence or absence of auxiliary cells; (iv) spore dimensions; (v) spore color; (vi) spore ornamentation; (vii) number and type of spore walls; and (viii) histochemical reactions (Hall, 1984; Morton, 1988, 1995; Schenck and Yvonne, 1992).

Spores of several species of VAM fungi readily germinate on distilled water or semi-solid water agar, suggesting that nutritional requirements for germination are met by the mobilization of spore reserves. In some instances, an exogenous supply of nutrients may result in increased germination rates; however, no specific requirement for germination on water agar has been reported. The germination rates of spores of VAM fungi are improved by thiamine, nutrient broth medium, and soil extracts, root exudates, soil volatile compounds and small amounts of glucose (Carr et al., 1985; Carr et al., 1986; Elias and Safir, 1987; Graham, 1982; Hepper, 1979, 1983, 1984; Mosse, 1959; Smith and Gianinazzi-Pearson, 1988). Some early biochemical events in the germination of VAM fungal spores have been studied. A number of enzyme activities have been demonstrated in germinating spores: glutamate dehydrogenase suggesting amino acid respiration; succinate dehydrogenase suggesting the Krebs (TCA) cycle; glyceraldehyde-3-phosphate dehydrogenase indicating the Embden-Myerhof-Parnas glycolytic pathway; and glucose 6-phosphate dehydrogenase, which suggests the presence of the hexose monophosphate shunt. However, it is necessary to demonstrate all the relevant enzymes of these pathways to confirm their full metabolic functions (Beilby, 1982, 1983; Macdonald and Lewis, 1978). Acetate is incorporated into organic and amino acids, indicating that the TCA cycle and amino acid biosynthetic pathways are operative. Nuclear DNA synthesis has not been detected during germination, but nuclear division does occur (Burggraffand Beringer, 1989; Smith and Gianinazzi-Pearson, 1988).

In summary, spores of VAM fungi seem to be able to germinate readily, but not continuous growth and sporulation unless the fungal hyphae form symbiotic relationship with living roots. During root-fungus interactions, signal molecules from host plants are probably produced to turn on the fungal genes for growth and development. The symbiotic biology involved should be a focus of study in order to design artificial systems for cultivation of VAM fungi in large quantities (Smith and Read,1997; Hirsch and Kapulnik, 1998; Harrison, 1999).

Progress toward the culture of VAM fungi will be possible if systematic studies of the interactions between the fungi and their host plants are made. In this regard, biochemical and molecular events of the symbiosis between nitrogen fixing rhizobia and the roots of legume plants, the most understood system in detail, is highly instructive and relevant to the symbiosis between mycorrhizal fungi and host roots. In nitrogen fixation, expression of bacterial nod genes, which are essential to the initial step in the nodulation processes, is induced by root exudate. The active compounds in the exudates have been identified to be flavonoids or isoflavonoids (Long, 1989; Hirsch and Kapulnik, 1998; Vierheilig et al., 1998). Pea mutants, which do not form root nodules when inoculated with rhizobia, are designated as nod negative. The connection between symbiotic nitrogen fixation and mycorrhizal symbiosis has been established by the finding that certain nod pea mutants have been found to also be myc negative (inability to form vesicular-arbuscular mycorrhiza) (Duc et al., 1989). This discovery suggests that several early steps in the processes of forming nodules on one hand and mycorrhizae on the other may involve common plant functions. To test the hypothesis that root exudates and flavonoids may be signal molecules in the early interactions between the fungi and the host plants, the effect of these bioactive chemicals on spore germination and rate of hyphae growths were investigated. Both root exudates and selected flavonoids significantly increased the frequency of spore germination and the rate of hyphal growth. The sensitivity of VAM fungi to small amounts (0.5 to 1.5 $\mu$M) of bioactive molecules suggests that flavonoids may acts as signals to induce VAM fungal development in the early stages of the symbiosis (Gianinazzi-Pearson et al., 1989; Hirsch and Kapulnik, 1998; Harrison, 1999).

VAM inocula are likely to play an increasingly important role in agriculture because their presence would not only reduce the use of applied fertilizers and pesticides but would also increase the resistance of plants to environmental and biological stresses (Cooper, 1987, Dehn, 1987, Hayman, 1987, Nelson, 1987). Current supplies of fungal inocula for experimental work are produced in pot cultures containing soil and whole plants. The resulting spores and propagules are contaminated with a variety of adventitious microorganisms.

Cultivation of VAM fungi under axenic conditions has been attempted without success for many years (Smith and Gianinazzi-Pearson, 1988). Production of VAM fungi on an industrial scale has not been feasible up to the present time because practical methods of cultivating VAM fungi have not been discovered. This is one of the key challenges for utilization of VAM fungi.

Hairy root organ culture of carrot, produced by transforming carrot slices of Ri plasmid (Ri, root inducing) of *Agrobacterium rhizogenes*, can be easily propagated and maintained. Hence, it may be used to monitor interaction of roots with VAM fungi. Becard and Fortin (1988) demonstrated that infectious spores of *Gigaspora margarita* were produced in hairy root tissue culture. Mugnier and Mosse (1987) have successfully used Ri T—DNA transformed morning glory roots as host for the colonization of VAM fungi. The hairy roots may provide an ideal system for supporting the cultivation of VAM fungi.

Mugnier (U.S. Pat. No. 4,599,312) discloses a method of producing endomycorrhizal fungi with vesicles and arbuscules in vitro by producing dicotyledonous roots that have been genetically converted by inserting genes of root-inducing or tumor-inducing plasmid into the genome of dicotyledonous roots, and then inoculating the transformed roots with endomycorrhizal spores.

Fortin (U.S. Pat. No. 5,554,530) discloses an aseptic method of producing VAM propagules by infecting transformed roots in vitro in a two-compartment container.

Sylvia et al. (U.S. Pat. No. 5,096,481) discloses a VAM inoculum composition comprising host root plants colonized by a least one species of VAM, the colonized roots having a particle size in the range of from about 33 $\mu$m to about 425 $\mu$m and a propagule density of up to about 1,000,000 VAM fungal propagules per gram dry mass of host plant root and method for encapsulating the composition and methods for enhancing plant growth utilizing the inocula. The method taught by Sylvia et al. is not aseptic as the method of the present invention.

Wood et al. (EP-209,627) disclose a method of producing fungal inoculum grown in axenic root organ cultures produced in porous substrates wetted with solutions. This procedure produces a small number of spores in the order of 83 spores per 30 ml of medium.

Okii (U.S. Pat. No. 4,945,059) disclose a method of proliferating VAM spores using potato roots and a porous amphoteric ion exchanger. This method is not aseptic as the method of the present invention.

Mosse et al. (U.S. Pat. No. 4,294,037) disclose a method of producing VAM fungi on plant roots in nutrient film culture. The technique requires continuous re-cycling of a large volume of nutrient liquid in a film which flows over the roots of plants. The present invention does not require large volumes of nutrient media for the production of VAM.

Several patents disclose various methods of dispersing VAM. Tuse et al. (U.S. Pat. No. 5,344,471) teach coating compositions comprising a polymer, VAM propagules, and a fungicide that selectively inhibits pathogenic fungi and several methods of coating roots with such compositions. Warner (U.S. Pat. No. 4,551,165) describes seed pellets made of a mixture of peat, a binder, seed, and VAM. Janerette (U.S. Pat. No. 5,178,642) teaches fungal inoculants made of a particulate carrier and a nutrient solution.

There is not disclosed a method for a continuous, aseptic in vitro production of VAM, *Glomus intraradices*, in particular.

SUMMARY OF THE INVENTION

The present invention is directed to novel fungal growth media.

The present invention shows the successful mass production of biologically active spores of vesicular arbuscular mycorrhizae (VAM) in an axenic transformed dicotyledonous root organ culture.

An object of the invention is to provide a method for the in vitro mass production of VAM, mainly spores.

Another object of the invention is to provide a method for the in vitro mass production of *Glomus intraradices*, mainly spores.

A further object of the present invention is to provide for the in vitro aseptic mass production of VAM (*Glomus intraradices*, in particular), mainly spores, which are contamination-free, simple, inexpensive, and effective.

Another object of the invention is to provide for axenic growth of continuous cultures of VAM (*Glomus intraradices*, in particular).

Still another object of the invention is to provide for conditions that will promote spore production of VAM (*Glomus intraradices*).

A further object of the invention is to provide for compositions comprising biologically pure cultures of VAM (*Glomus intraradices*, in particular), propagated by the methods of the invention. The composition may comprise a biodegradable material suitable as a carrier in the composition, including peat moss, vermiculite, perlite, alginate polymer, and xanthan-chitosan complex etc. These compositions may also comprise isoflavonoids, alkali formononetinate, or both.

The invention provides for a method of proliferating VAM (*Glomus intraradices*, in particular) by inoculating the VAM fungi directly on or around the roots of plants including: citrus, such as orange; fruits, such as strawberry; ornamental plants, such as rose; fruit and nut trees; specialty crops, such as ginseng; artificial seeds such as alfalfa embryos; crops, such as soybean, wheat, and corn; and plantlets grown from tissue culture.

DETAILED DESCRIPTION OF THE INVENTION

General Definitions

Wet sieving is the process of passing spores collected from the roots of potted plants or soil samples in an aqueous solution through a sequence of sieves having decreasing pore sizes ranging from 1,000 $\mu$m to 75 $\mu$m.

Subculture is the process of renewing or refreshing the culture by transferring a small portion of the cells to fresh medium.

The compositions of the fungal growth media of the present invention are as follows:

| Chemical: | Range | Optimum |
| --- | --- | --- |
| $Ca(NO_3)_2.4H_2O$ | 300–500 mg/l | 472 mg/l |
| $CaCl_2.2H_2O$ | 60–90 mg/l | 74 mg/l |
| $MgSO_4.7H_2O$ | 450–600 mg/l | 493 mg/l |
| $KNO_3$ | 80–120 mg/l | 100 mg/l |
| $KH_2PO_4$ | 2–5 mg/l | 3 mg/l |
| Ca phytate | 5–20 mg/l | 10 mg/l |
| NaFeEDTA | 6–10 mg/l | 8 mg/l |
| $MnCl_2.4H_2O$ | 3–6 mg/l | 4 mg/l |
| $ZnSO_4.7H_2O$ | 2–3 mg/l | 2 mg/l |
| $CuSO_4.5H_2O$ | 0.05–0.15 mg/l | 0.1 mg/l |
| KI | 0.5–0.8 mg/l | 0.6 mg/l |
| $H_3BO_3$ | 1–2 mg/l | 1.5 mg/l |
| $Na_2MoO_4.2H_2O$ | 0.003–0.006 mg/l | 0.005 mg/l |
| myoinositol | 20–50 mg/l | 30 mg/l |
| thiamine | 0.1–0.4 mg/l | 0.2 mg/l |
| nicotinic acid | 0.5–1.0 mg/l | 0.5 mg/l |
| pyridoxine | 0.1–0.5 mg/l | 0.1 mg/l |
| glycine | 2 mg/l to 4 mg/l | 3 mg/l |
| carbenicillin | 20–80 mg/l | 50 mg/l |
| Sucrose | 7.5–10 g/l | 8 g/l |
| gellan gum | 3 g/l to 5 g/l | 4 g/l |
| pH | 5.5–6.5 | 6.0 |

The gellified medium used may be gellan gum, agar, agarose, Phytagel™ (Sigma, St. Louis, Mo., USA), or Gel-Gro. The gellified medium used here was gellan gum and more specifically the trade name of Gel-Gro (ICN Biochemicals, Cleveland, Ohio 44128, USA). However, any gel material with similar properties may be used.

Compositions comprising biologically pure cultures of VAM (*Glomus intraradices*, in particular), may be propagated by growing fungi in the fungal media in the presence of transformed dicotyledonous roots described above. The composition may comprise a biodegradable material suitable as a carrier in the composition, including peat moss, vermiculite, perlite, alginate polymer, and xanthan-chitosan complex etc. These compositions may also comprise isoflavonoids, alkali formononetinate, or both.

An in vitro system using Agrobacterium-transformed dicotyledon root and vesicular-arbuscular mycorrhizal fungi was developed to produce viable and aseptic spores by growing cultures in the fungal growth media of the present invention. The dicotyledon used may be carrot, tomato, strawberry, morning glory, or clover. The entire life cycle from the growth of initial germ tubes to the formation of external mycelium network and spore production was observed nondestructively using light microscopy. The system may be subcultured continuously following the establishment of fungal growth on roots for production of viable and clean spores in the defined media of the present invention using Petri dishes at ambient temperatures. The system is easy and simple to handle and does not require expensive and complicated facilities for the production of large quantities of VAM inocula.

The invention provides a method of producing aseptic, biologically pure fungal spores, the method comprising: cultivating aseptically transformed dicotyledon root organs capable of autonomous growth in vitro in media comprising $Ca(NO_3)_2$, $CaCl_2$, $MgSO_4$, $KNO_3$, $KH_2PO_4$, Ca phytate, NaFeEDTA, $MnCl_2$, $ZnSO_4$, $CuSO_4$, KI, $H_3BO_3$, $Na_2MoO_4$, myoinositol, thiamine, nicotinic acid, pyridoxine, glycine, carbenicillin, sucrose, and gellified medium; inoculating the transformed root organs with endomycorrhizal fungal spores; cultivating the inoculated transformed root organs for a time sufficient for the production of endomycorrhizal fungal spores; and recovering the endomycorrhizal spores from the medium.

EXAMPLE

Transformation of Carrot by *Agrobacterium hizogenes*

Ten-inch long carrots (*Daucus carr carota* L.) were surface sterilized by soaking in 70% (v/v) ethanol for three minutes and then in 15% (v/v) Clorox for 15 minutes and rinsing in sterile distilled water several times. The basal 2 cm portion of the root was discarded and 5 mm thick discs were cut by transverse section, proceeding toward the apex of the root. The slices were immediately placed on 1% water agar (10 gram of DIFCO agar in one liter of distilled water) in Petri dishes with the apical surface facing up. The carrot slice was inoculated with *Agrobacterium rhizogenes* strain A4, TR7, or 8196. The inocula were grown on nutrient agar for three days. One loopful of bacteria (approximately $10^9$ cells) was evenly spread on the cambial area of the carrot, then placed on water agar and incubated at 28° C. in the dark. After four weeks, numerous adventitious roots (hairy roots) emerged because these carrot cells were transformed via integration of the root-inducing (Ri) plasmid of *A. rhizogenes* into the plant genome.

Aseptic Hairy Root Organ Cultures

A few transformed roots proliferating among the massive hairy roots were gently picked using sterile forceps and placed on White's medium containing carbenicillin (500 μg/ml) and 1% agar in petri dishes for four weeks. The roots were then subcultured several times in the presence of carbenicillin. The resulting bacteria-free root organ cultures may be maintained indefinitely on medium without antibiotics.

Sterilization of VAM Fungal Spores

The preparation of spores completely free from any microbial contamination is crucial for successful cultivation of VAM fungi in root organ cultures. Spores of *Glomus intraradices* Schenck & Smith were used in these experiments. Spores were produced in pots with sorghum as host in a greenhouse and were recovered from potting soil by wet sieving through screens. Spores were first washed with 0.05% Tween 20 and decontaminated in 2% chloramine T for ten minutes twice consecutively. The spores were then rinsed in antibiotic solution of streptomycin (200 μg/ml) and gentamycin (100 μg/ml) four times and stored in antibiotic solution for one week. A second round of decontamination was carried out as described above by treatment with chloramine T and antibiotics. The spores were spread out on water agar and stored at 4° C. Spores may be stored in this way for up to three months without losing their viability. Individual spores may be picked up for experiments using a scalpel under a dissecting microscope in a laminar flow hood.

Initiation of Dual Culture System

Ten spores of *Glomus intraradices* were placed in the center of the Petri dish containing the fungal medium solidified with gellan gum and were incubated at 28° C. for five days. Then a 10 cm-root segment, which was pre-grown in the fungal growth medium for one week, was placed near the emerging germ tube of the spore. The proximal end of the root tip is oriented towards the tip of germ tube. The inoculated roots were incubated in the dark at 28° C. The Petri dish was observed periodically for the growth of external hyphae and sporogenesis.

Developmental Stages of VAM Fungal Growth

Figure 1:
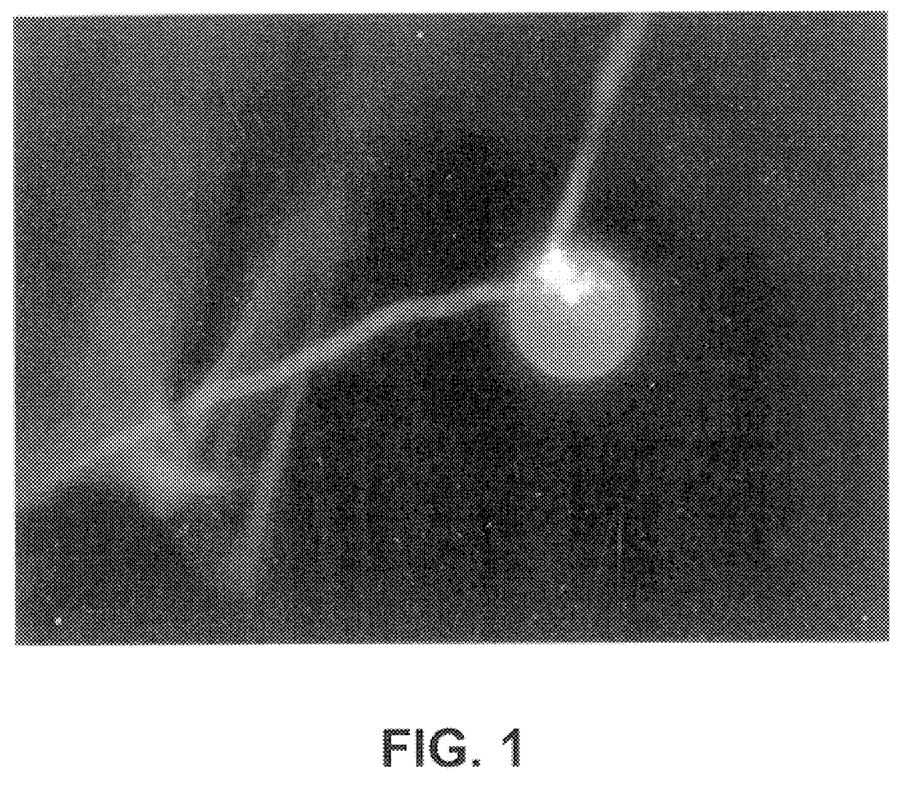
FIG. 1 is a photograph of a germinated *Glomus intraradices* spore (seen as a large, white sphere) grown on the fungal growth medium described herein. The photograph shows the migration of individual nuclei of a typical multinucleate spore, stained with a fluorescent dye [4,6-diamidino-2-phenylindole (DAPI)], through hyphal extensions, magnified approximately 600×.
Figure 2:
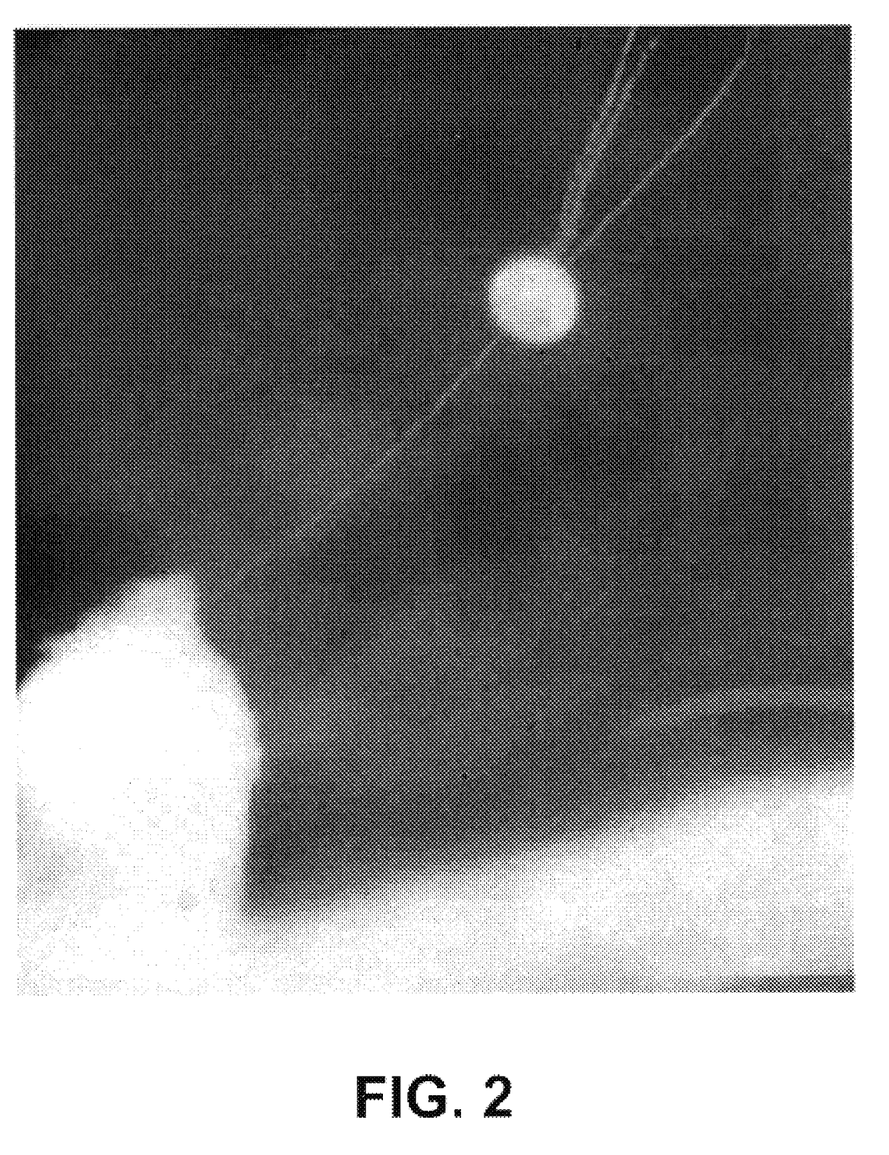
FIG. 2 is a photograph of a germinated *Glomus intraradices* spore (seen as a white sphere), grown on the fungal growth medium of the present invention. The photograph illustrates the movement of the hyphae towards a dicotyledonous (carrot) root tip (seen on the bottom as a white area), magnified approximately 200×.
Figure 3:
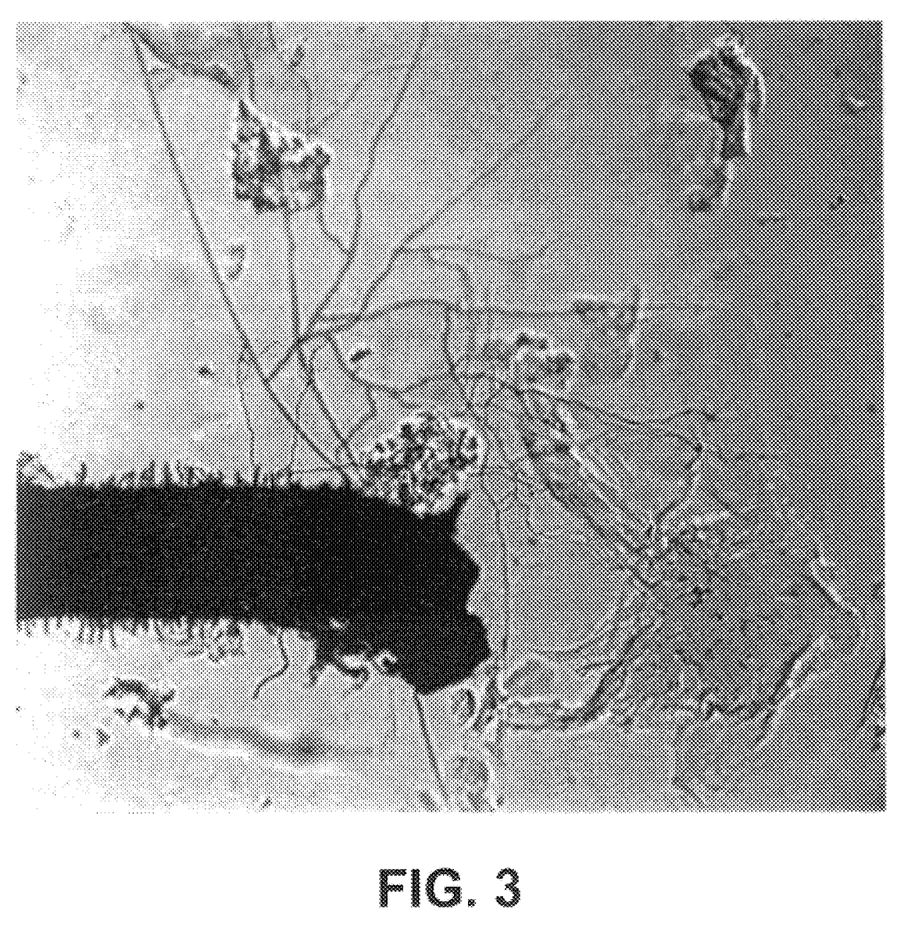
FIG. 3 is a photograph of infected root tips, which stimulate hyphal growth, magnified approximately 100×.
Figure 4:
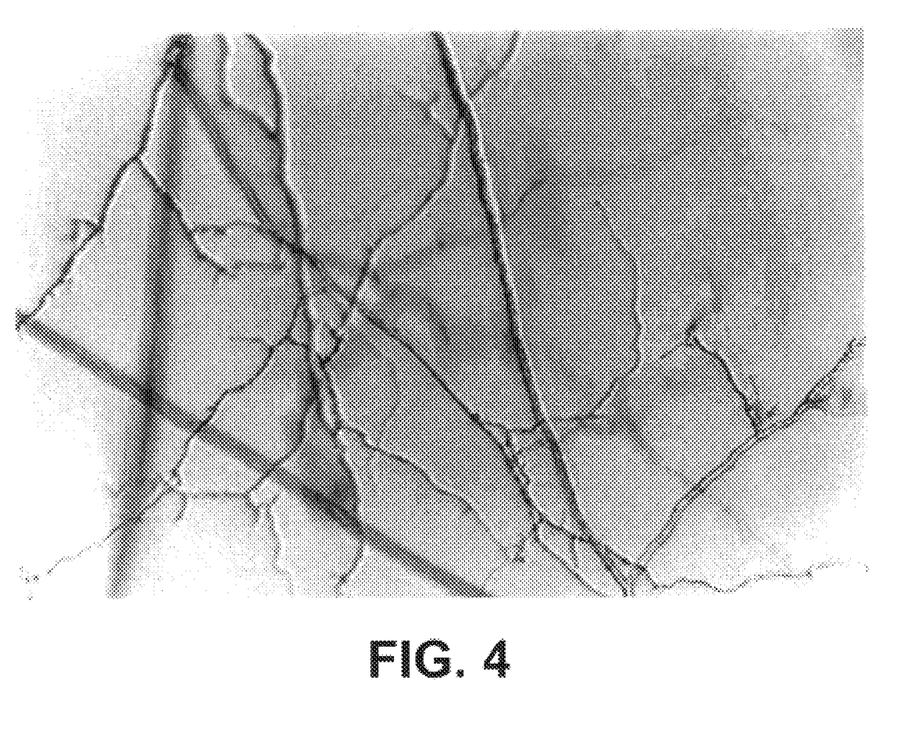
FIG. 4 is a photograph of *Glomus intraradices* hyphal proliferation resulting in a network structure, magnified approximately 100×.
Figure 5:
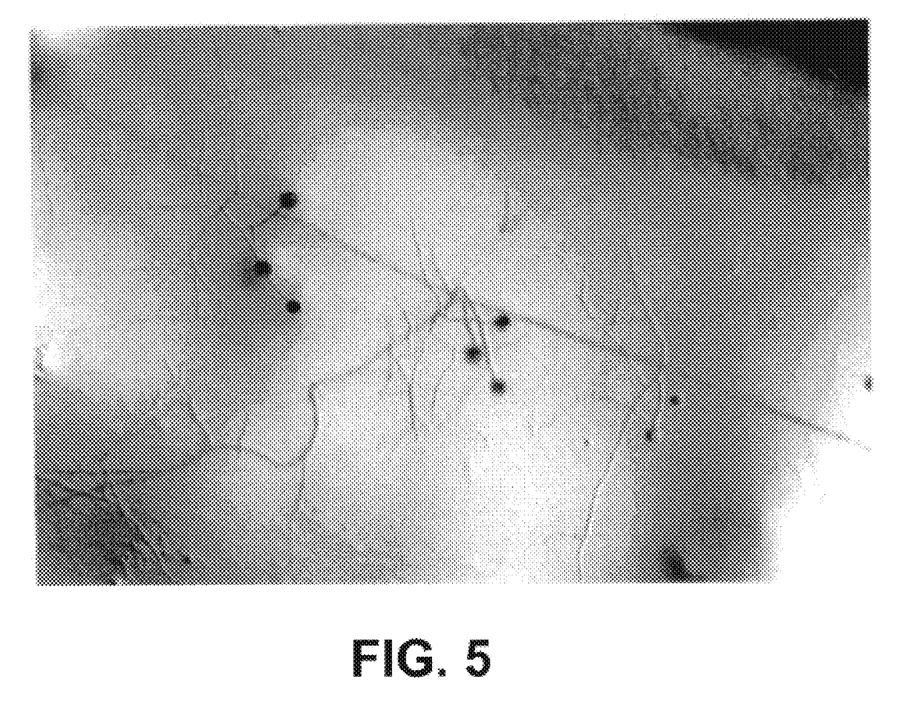
FIG. 5 is a photograph of the formation of small vegetative spores of *Glomus intraradices* (seen as dark spheres attached at the end of individual hyphae), magnified approximately 100×.
Figure 6:
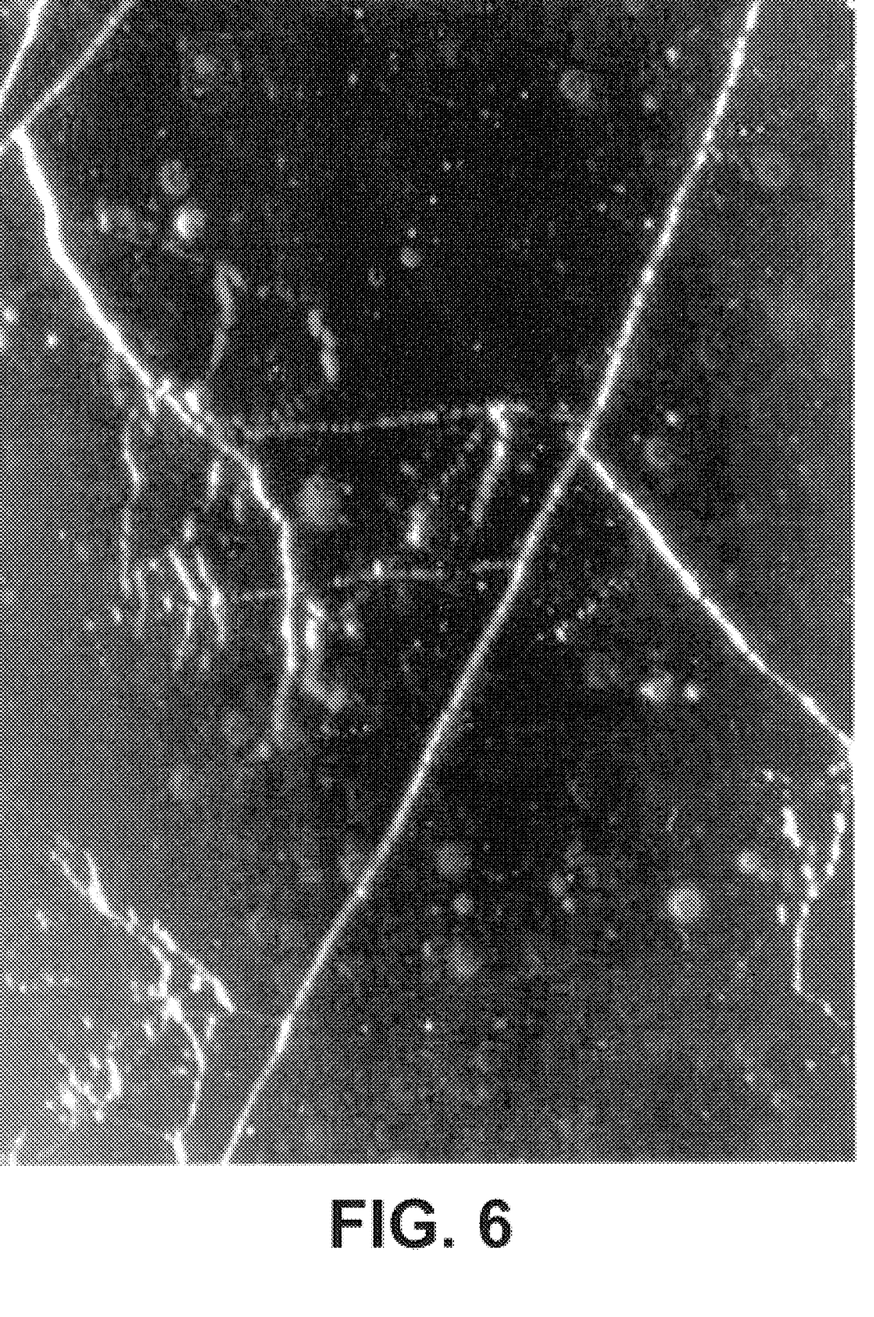
FIG. 6 is a photograph illustrating the high density of *Glomus intraradices* spres (seen as dark spheres) after three months of growth on the medium of the present invention, magnified approximately 100×.
Figure 7:
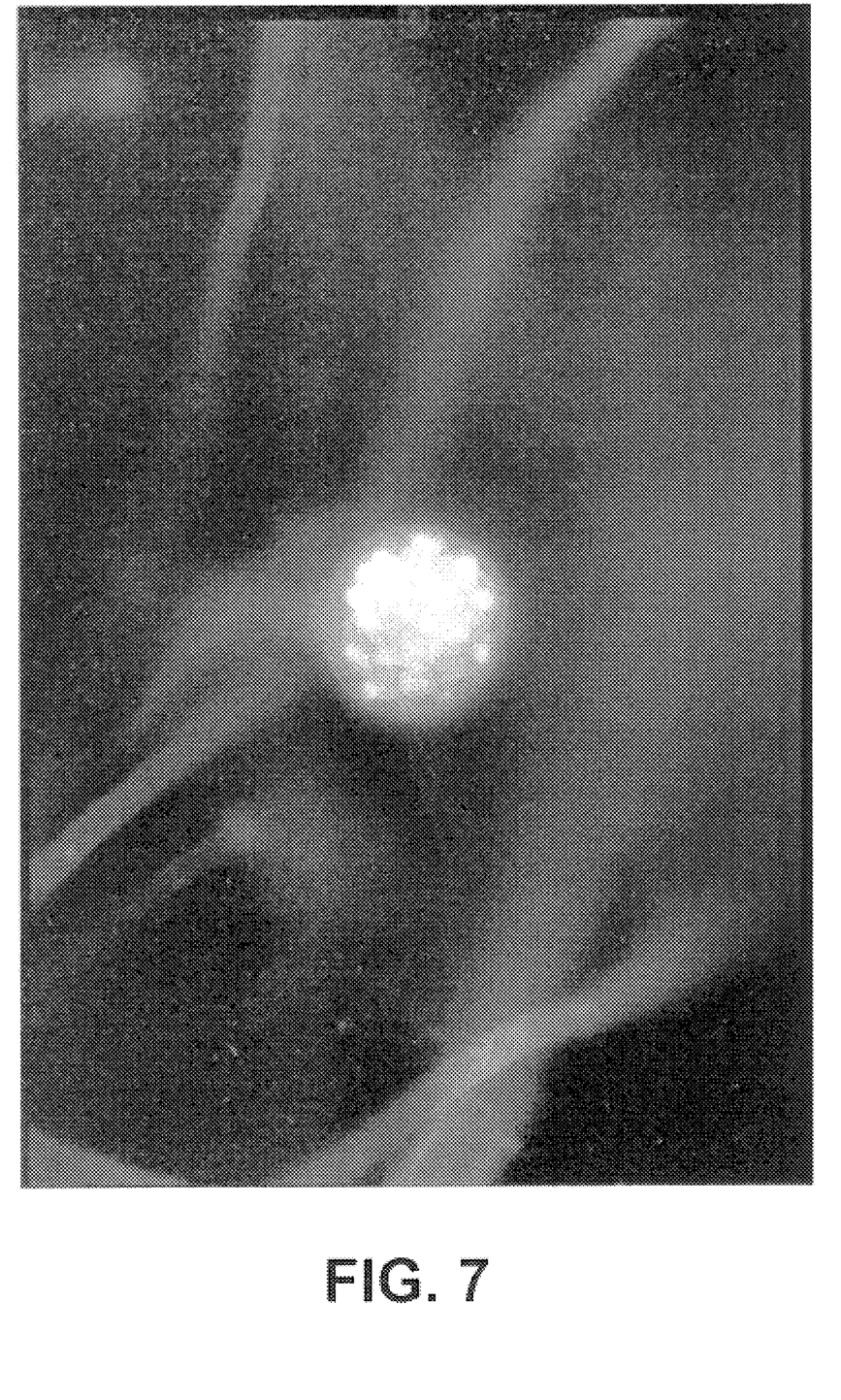
FIG. 7 is of a DAPI-stained *Glomus intraradices* spore having many nuclei (seen as fluorescent spheres inside the spore), magnified approximately 600×.

The VAM fungus *G. intraradices* was used in the experiments. All the stages occurring in the development of VAM fungal infections in whole plants have been found in root organ culture. The advantage of dual culture in a Petri dish is that the progress on extraradical fungal development may be easily, frequently, and non-destructively observed with a microscope. An increase in germ tube growth was observed in pre-germinating spores when placed near growing roots. The attachment of germ tubes to the root surface, followed by highly branched hyphal growth, results in a fan-like structure (FIG. 3). Rapid growth of extraradical fungal growth (FIG. 4) and formation of small vegetative spores (FIG. 5) were seen directly under a microscope. Secondary infections on growing roots were formed and the VAM fungal hyphae spread all over the entire Petri dish in high density, followed by spores formation within three weeks after the initiation of the dual culture system. At the end of the three month period, the number of spores ranged from at least 1,000 to 2,000 per Petri plate. Spore sizes were comparable to those of typical *G. intraradices* described in the literature (FIG. 1). The diameters of the spores were approximately 100 μm.

Continuous Propagation of Dual VAM-root Culture by Subculturing

Four- to five-month-old dual cultures of *G. intraradices* in fungal growth medium of the present invention were successfully used as the starting material for subculture. The entire gel was cut into sixteen pie-shaped pieces; each slice was transferred to a Petri dish containing the fungal growth medium. The roots and VAM fungi started to grow further immediately, the fungal hyphae grew all over the gel along with new growth of the roots. One to two thousand spores were produced in ten weeks. The dual culture could be continuously propagated to produce large numbers of spores. The dual cultures of VAM and transformed carrot root were propagated for six years and can probably be continued indefinitely. The size of the spores are the same as the original spores used to inoculated the root organ cultures.

The procedure described above produced genetically transformed hairy carrot root-organ cultures and overcame a number of technical barriers to initiate vesicular-arbuscular mycorrhizal (VAM) symbiosis with the transformed roots. Mycorrhizal roots were formed and could grow in a chemically defined medium, thereby allowing consistent production of at least 1,000 to 2,000 fungal spores per Petri dish. The most striking feature of the system is that the dual cultures can be subcultured, generation after generation, and produce abundant aseptic spores. The spores are important inocula for the horticulture, field and specialty crop plants to form beneficial VAM symbiosis. The fungal material produced by the methods of the present invention allows for both the transformed roots and the spores to be used as inocula.

Biological Activity of the Spores Produced in the Dual Culture System

The spores produced on root organ culture are free from other contamination of microorganisms. The spores can be used as inocula to start new dual cultures. The spores can also to be used to inoculate seedlings of sorghum plants growing in sterile, phosphate deficient soil. Many new spores were found in soil samples within five months after inoculation.

REFERENCES

Al-Karaki G N, AlRaddad A, Clark R B. 1998. Water stress and mycorrhizal isolate effects on growth and nutrient acquisition of wheat. J. Plant Nutr. 21: 891–902.

Azcón-Aguilar C, Barea J M. 1996. Arbuscular mycorrhizas and biological control of soil-borne plant pathogens—an overview of the mechanisms involved. Mycorrhiza 6(6): 457–464.

Becard G, Fortin J A (1988) Early events of vesicular-arbuscular mycorrhiza formation on Ri T-DNA transformed roots. Phytochem. 108:211–218.

Chabot S (1990) Systeme axenique de culture en duo comme modele pour leetude des endomycorhizes a vesicules et arbuscules. Memoire M. Sc. Universite Laval.

Cooper K M (1984) Physiology of VA mycorrhizal associations. In: VA Mycorrhizal (C. L. Powell and D. J. Bagyaraj, eds.). CRC Press, Inc. Boca Raton, Fla. pp. 155–186.

Dehne H W (1982) Interactions between vesicular-arbuscular mycorrhizal fungi and plant pathogens. Phytopathology 72:1115–1119.

Danneberg,G.; Latus,C.; Zimmer,W.; Hundeshagen,B.; Schneider-Poetsch,H J., Bothe,H. (1992)—Influence of vesicular-arbuscular mycorrhiza on phytohormone balances in maize (Zea mays L.)—J. Plant Physiol. 141, 33–39.

Dixon R K.1990. Cytokinin activity in Citrus jambhiri seedlings colonized by mycorrhizal fungi. Agric Ecosyst Environ. 29: 103–106.

Gemma J N, Koske R E (1988) Pre-infection interactions between roots and the mycorrhizal fungus Gigaspora gigantea: chemotropism of germ tubes and root growth responses. Transactions of the British Mycological Society, 91, 123–132.

Gerdemann J W, Nicolson T H (1963) Spores of mycorrhizal Endogone species extracted from soil by wet sieving and decanting. Transactions of the British Mycological Society, 46, 235–244.

Ginzberg I, David R, Shaul O, Elad Y, Wininger, S, Ben-Dor B, Badani H, Fang Y W, Van Rhijn P, Li Y, Hirsch A M, Kapulnik Y. 1998. Glomus intraradices colonization regulates gene expression in tobacco roots. Symbiosis 25:145–157.

Goicoechea N, Antolin M C, Strnad M, Sanchez-Diaz M. 1996. Root cytokinins, acid phosphatase and nodule activity in drought-stressed mycorrhizal or nitrogen-fixing alfalfa plants. J Exp Bot. 47(298): 683–686.

Goicoechea N, Dolezal K, Antolin M C, Strnad M, Sanchez-Diaz M. 1995. Influence of mycorrhizae and Rhizobium on cytokinin content in drought-stressed alfalfa. J Exp Bot. 46(291): 1543–1549.

Gianinazzi S, Schhepp H. 1994. Impact of Arbuscular Mycorrhizas on Sustainable Agriculture and Natural Ecosystems. Birkh@user Verlag, Basel, Switzerland. 226 pp. ISBN 3-7643-5000-8.

Hall I R (1984) Taxonomy of VA mycorrhizal fungi. In VA Mycorrhizae (C. L. Powell and D. J. Bagyaraj, eds.). CRC Press, Inc. Boca Raton, Fla. pp. 57–94.

Harley J L, FRS, Smith S E (1983) Mycorrhizal Symbiosis. Academic Press.

Hayman D S 1987 VA mycorrhizas in field crop system. In VA Mycorrhizae (C. L. Powell and D. J. Bagyaraj, eds.). CRC Press, Inc. Boca Raton, Fla., pp. 71–91.

Harrison M J. 1999. Molecular and cellular aspects of the arbuscular mycorrhizal symbiosis. Annu. Rev. Plant Physiol. Plant Molec. Biol. 50: 361–389.

Hirsch, A. M. and Kapulnik, Y. 1998. Signal transduction pathways in mycorrhizal associations: Comparisons with the Rhizobium-legume symbiosis. Fungal Genet. Biol. 23: 205–212.

Hua S-ST 1989 Initial interaction of vesicular-arbuscular mycorrhizal fungus and carrot hairy root. Plant Physiol. 89:86.

Hua S-ST 1990 Developmental responses of vesicular-arbuscular mycorrhizal fungi to symbiotic plant hosts. Abstracts of the 90th Annual Meeting of ASM. p. 252.

Hua S-ST 1990 Prospects of axenic growth and feasibility of genetic modification of vesicular-arbuscular mycorrhizal fungi. 8th North America Conference of Mycorrhizae.

Mendoza, J; Borie, F. 1998. Effect of Glomus etunicatum inoculation on aluminum phosphorus, calcium, and magnesium uptake of two barley genotypes with different aluminum tolerance. Commun. Soil Sci. Plant Anal. 29: 681–695.

Monnier M. 1976. Culture in vitro de l'embryon immature de Capsella bursa-pastoris. Maench.Revue de Cytologie and Biologie Vegetale, 39, 1–120.

Morton, J. B. 1995. Taxonomic and phylogenetic divergence among five Scutellospora species (Glomales, Zygomycetes) based on comparative developmental sequences. Mycologia 87:127–137.

Mosse B. 1962. The establishment of vesicular-arbuscular mycorrhiza under aseptic conditions. J. of Gen. Microbiol. 27, 509–520.

Mugnier J and Mosse B 1987 Vesicular-arbuscular mycorrhizal infection in transformed root-inducing T.-DNA roots grown axenically. Phytopathology 77:1045–1050.

Muller, J. 1999. Mycorrhizal fungal structures are stimulated in wildtype peas and in isogenic mycorrhiza-resistant mutants by tri-iodo-benzoic acid (TIBA), an auxin-transport-inhibitor. Symbiosis 26: p 379–389.

Pfleger F L, Linderman R G. 1994. Mycorrhizae and Plant Health. APS Press, St. Paul, Minn. 344 pp. 0-89054-158-2.

Podila G K, Douds D D. 1999. Current Advances in Mycorrhizae Research. American Phytopathological Society Press. Proceedings of the Symposium "Integrating principles of plant pathology and molecular biology with mycorrhiza research", American Phytopathological Society meeting, November, 1998.

Nelsen C E 1987 The water relations of vesicular-arbuscular mycorrhizal systems. In VA Mycorrhizae (C. L. Powell and D. J. Bagyaraj, eds.). CRC Press, Inc. Boca Raton, Fla. pp. 71–91.

Ryder M H, Tate M E, Kerr A 1985 Virulence properties of strains of Agrobacterium on the apical and basal surfaces of carrot root discs. *Plant Physiol.* 71:215–221.

Schenck N C; Perez Yvonne. 1992. Methods Manual for VA Mycorrhizae. Synergistic-Publications 250p.

Smith S E, Gianinazzi-Pearson. 1988. Physiological interactions between symbionts in vesicular-arbuscular mycorrhizal plants. *Ann. Rev. Plant Physiol. & Plant Mol. Biol.* 39:221–244.

Smith S E, Read D J. 1997. *Mycorrhizal Symbiosis*. 2nd ed. Academic Press, London. 605 pp.

Sturmer, S. L. and J. B. Morton. 1997. Developmental patterns defining morphological characters in spores of species in Glomus (Glomales, Zygomycetes). *Mycologia* 89:72–81.

Tepfer D 1984 Transformation of several species of high plants by *Agrobacterium rhizogenes*: sexual transmission of the transformed genotype and phenotype. *Cell* 37:959–967.

Vierheilig H. Bago B. Albrecht C, Poulin M J, Piche Y. 1998. *Flavonoids and arbuscular mycorrhizal fungi In: Flavonoids in the Living System*; Eds. Manthey J, Buslig B. Plenum Press, New York; p. 9–33.

White P R 1963 In: *The cultivation of animal and plant cells*. 2nd edition. Ronald Press, New York.

The references cited above and throughout the specification are incorporated by reference in their entirety.

What is claimed is:

1. A fungal growth medium comprising medium components in the following ranges: hydrated $Ca(NO_3)_2$, 300–500 mg/l; $CaCl_2.2H_2O$, 60–90 mg/l; $MgSO_4.7H_2O$, 450–600 mg/l; $KNO_3$, 80–120 mg/l; $KH_2PO_4$, 2–5 mg/l; Ca phytate, 5–20 mg/l; NaFeEDTA, 6–10 mg/l; $MnCl_2.4H_2O$, 3–6 mg/l; $ZnSO_4.7H_2O$, 2–3 mg/l; $CuSO_4.5H_2O$, 0.05–0.15 mg/l; KI, 0.5–0.8 mg/l; $H_3BO_3$, 1–2 mg/l; $Na_2MoO_4.2H_2O$, 0.003–0.006 mg/l; myoinositol, 20–50 mg/l; thiamine, 0.1–0.4 mg/l; nicotinic acid; 0.5–1.0 mg/l; pyridoxine, 0.1–0.5 mg/l; glycine, 2 mg/l to 4 mg/l; carbenicillin, 20–80 mg/l; sucrose, 7.5–10 g/l; and gelling agent, 3 g/l to 5 g/l, and wherein phosphorus in the medium is in the range of 0.022 mmolar to 0.065 mmolar.

2. The growth medium of claim 1, wherein the medium comprises: hydrated $Ca(NO_3)_2$, 472 mg/l; $CaCl_2.2H_2O$, 74 mg/l; $MgSO_4.7H_2O$, 493 mg/l; $KNO_3$, 100 mg/l; $KH_2PO_4$, 3 mg/l; Ca phytate, 10 mg/l; NaFeEDTA, 8 mg/l; $MnCl_2.4H_2O$, 4 mg/l; $ZnSO_4.7H_2O$, 2 mg/l; $CuSO_4.5H_2O$, 0.1 mg/l; KI, 0.6 mg/l; $H_3BO_3$, 1.5 mg/l; $Na_2MoO_4.2H_2O$, 0.005 mg/l; myoinositol, 30 mg/l; thiamine, 0.2 mg/l; nicotinic acid, 0.5 mg/l; pyridoxine, 0.1 mg/l; glycine, 3 mg/l; carbenicillin, 50 mg/l; sucrose, 8 g/l; and wherein said gelling agent is gellan gum, 4 g/l.

3. The medium of claim 1, wherein said gelling agent is gellan gum.

4. A dry preparation for mixing with water to form a fungal growth medium, comprising medium components in the following ranges: hydrated $Ca(NO_3)_2$, 300–500 mg/l; $CaCl_2.2H_2O$, 60–90 mg/l; $MgSO_4.7H_2O$, 450–600 mg/l; $KNO_3$, 80–120 mg/l; $KH_2PO_4$, 2–5 mg/l; Ca phytate, 5–20 mg/l; NaFeEDTA, 6–10 mg/l; $MnCl_2.4H_2O$, 3–6 mg/l; $ZnSO_4.7H_2O$, 2–3 mg/l; $CuSO_4.5H_2O$. 0.05–0.15 mg/l; KI, 0.5–0.8 mg/l; $H_3BO_3$, 1–2 mg/l; $Na_2MoO_4.2H_2O$, 0.003–0.006 mg/l; myoinositol, 20–50 mg/l; thiamine, 0.1–0.4 mg/l; nicotinic acid; 0.5–1.0 mg/l; pyridoxine, 0.1–0.5 mg/l; glycine, 2 mg/l to 4 mg/l; carbenicillin, 20–80 mg/l; surcose, 7.5–10 g/l; and gelling agent, 3 g/l to 5 g/l, and wherein phosphorus in the medium is in the range of 0.022 mmolar to 0.065 mmolar.

5. The preparation of claim 4, wherein the growth medium comprises: hydrated $Ca(NO_3)_2$, 472 mg/l; $CaCl_2.2H_2O$, 74 mg/l; $MgSO_4.7H_2O$, 493 mg/l; $KNO_3$, 100 mg/l; $KH_2PO_4$, 3 mg/l; Ca phytate, 10 mg/l; NaFeEDTA, 8 mg/l; $MnCl_2.4H_2O$, 4 mg/l; $ZnSO_4.7H_2O$, 2 mg/l; $CuSO_4.5H_2O$, 0.1 mg/l; KI, 0.6 mg/l; $H_3BO_3$, 1.5 mg/l; $Na_2MoO_4.2H_2O$, 0.005 mg/l; myoinositol, 30 mg/l; thiamine, 0.2 mg/l; nicotinic acid, 0.5 mg/l; pyridoxine, 0.1 mg/l; glycine, 3 mg/l; carbenicillin, 50 mg/l; sucrose, 8 g/l; and wherein said gelling agent is gellan gum, 4 g/l.

* * * * *